United States Patent [19]
Otten et al.

[11] Patent Number: 5,833,825
[45] Date of Patent: Nov. 10, 1998

[54] SILVER/SILVER CHLORIDE REFERENCE ELECTRODES HAVING SELF-CONTAINED CHLORIDE SOLUTION AND METHODS OF MAKING SAME

[75] Inventors: Sief Otten; Mark Lubin, both of Miami, Fla.

[73] Assignee: Upscale Technologies, Inc., Miami, Fla.

[21] Appl. No.: 798,361

[22] Filed: Feb. 10, 1997

[51] Int. Cl.$^6$ .................................................. G01N 27/26
[52] U.S. Cl. ........................................ 204/435; 204/415
[58] Field of Search ..................................... 204/435, 415

[56] References Cited

U.S. PATENT DOCUMENTS 4,053,381  10/1977  Hamblen et al. ........................ 204/435
5,346,604   9/1994  Van Sin et al. .......................... 204/415

OTHER PUBLICATIONS

Instruction sheet for Calomel Electrode K401 by Radiometer Copenhagen. No month or year available.
Instruction sheet for Silver Chloride Electrode K801 by Radiometer Copenhagen. No month or year available.
"Reference Electrode" by Radiometer Copenhagen. No month or year available.
"Choosing the Correct Reference System" by Orion Research, Inc. No month or year available.
Analytical Technological Inc., data sheet for ROSS™ electrodes, p. 19. No month or year available.
Analytical Technological Inc., data sheet for Orion™ electrodes, p. 21. No month or year available.
Phoenix Electrode Company, Glass and Reference Electrodes part no. and specification sheet, bulletin 0492. No month or year available.
Innovative Sensors, Inc., General Laboratory Electrodes specification sheet. No month or year available.
Microelectronics, Inc., Micro–Reference Electrodes specification sheet. No month or year available.
Microelectronics, Inc., Reference Electrodes and Carbon Dioxide Electrode specification sheet. No month or year available.
World Precision Instruments, Dri–Ref™ Reference Electrodes specification sheet. No month or year available.
Diamond General Corp., "Sensors That Mate With The Electrochem Analyzer And Chemical Microsensor II".
Diamond General Corp., "Polarographic Oxygen Electrodes". No month or year available.

*Primary Examiner*—Bruce F. Bell
*Attorney, Agent, or Firm*—David P. Gordon; David S. Jacobson; Thomas A. Gallagher

[57] ABSTRACT

A Ag/AgCl electrode includes a rigid tube within which a Ag/AgCl conductor is mounted by epoxy. An insulated wire lead is coupled by a solder joint to the Ag/AgCl conductor. An optional plastic cap seals the upper end of the tube and the wire lead extends out of the upper end of the tube and through the plastic cap. A sodium chloride solution is provided in the lower end of the tube such that the conductor is bathed in the solution. The solution is maintained within the tube by a porous glass, ceramic, or polymeric plug which is press fit into the lower end of the tube. The lower end of the tube, including the plug, is coated with a water soluble non-toxic substance. The water soluble coating is preferably made from a concentrated solution of polyvinyl alcohol (PVA) in deionized or RO water which is preferably applied by dip coating and air drying. The PVA forms a hard durable protective coating which prevents the sodium chloride solution from dissipating during the time between manufacture and use of the electrode. In addition, the PVA quickly dissolves once in contact with flowing water.

20 Claims, 1 Drawing Sheet

SILVER/SILVER CHLORIDE REFERENCE ELECTRODES HAVING SELF-CONTAINED CHLORIDE SOLUTION AND METHODS OF MAKING SAME

This application is related to co-owned application Ser. No. 08/758,584 filed Nov. 27, 1996, and co-owned U.S. Pat. No. 5,614,078, the complete disclosures of which are hereby incorporated by reference herein.

BACKGROUND OF THE INVENTION

1. Field of the Invention

The invention relates to reference electrodes which are used in electrochemical reactions. More particularly, the invention relates to Ag/AgCl electrodes which have a self-contained chloride solution and to methods for making such electrodes.

2. State of the Art

Co-owned U.S. Pat. No. 5,614,078 discloses methods and apparatus for the removal of nitrates from water. Although not limited thereto, the apparatus generally includes an electrochemical flow cell through which the aqueous solution containing nitrates flows or a holding tank cell into which the solution is introduced and then released after processing, and an electrode system including a carbon fiber cathodic electrode, a carbon fiber anodic electrode and a reference electrode. All of the electrodes are immersed in the aqueous solution and coupled to an electronic control circuit which impresses a voltage across the electrodes such that the voltage causes electrochemical reduction/oxidation reactions on the surfaces of the cathodic and anodic electrodes. According to the method, the electrodes are at a potential wherein nitrates are reduced to gaseous products but hydrogen, oxygen, chlorine, and other possibly noxious substances are not produced. According to the disclosed preferred embodiment, the reference electrode is a silver/silver-chloride electrode, the cathodic and anodic electrodes are carbon fibers based on polyacrylonitrile (PAN), and the surface area ratio of the anodic electrode to the cathodic electrode is preferably in the range of 40:1 to 120:1.

Co-owned Ser. No. 08/758,584 discloses a carbon fiber electrode which is coated with a noble metal oxide to effectively create a noble metal oxide electrode with a very large surface area. According to a disclosed preferred embodiment, the noble metal oxide is iridium oxide. A disclosed method of making the electrode includes preparing a solution of iridium chloride compound and isopropyl alcohol, dipping a carbon fiber electrode into the solution, drying the electrode in the presence of nitrogen, and heat treatment of the electrode in the presence of oxygen. The noble metal oxide electrodes are used in nitrate removal systems as described above.

The nitrate removal systems described in the above-referenced co-owned patent applications may be used to remove nitrates from either saltwater or fresh water. In relatively small saltwater systems, the reference electrode may be configured as a bare Ag/AgCl pellet or wire and its distance from the cathode is not critical since the cathode is relatively small. In relatively large saltwater systems, where the size of the cathode is relatively large, the control of the cathode voltage is significantly more critical. In these systems, the cathode and the reference electrode must be located very close to each other. Under these circumstances, a bare Ag/AgCl reference electrode cannot be used because of the danger of a short circuit. In fresh water systems of all sizes, a bare Ag/AgCl reference electrode cannot be used for two reasons. First, the absence of significant chloride levels in fresh water renders it significantly less conductive than saltwater. Consequently, the reference electrode must be placed very close to the cathode to assure that all parts of the cathode operate at the same electrode potential. Therefore, the danger of a short circuit is present. Second, the chloride levels in fresh water are unstable as well as low. Consequently, there is no constant reference potential for the reference electrode.

It is known in the art to provide a Ag/AgCl electrode with a self-contained chloride solution. Referring now to prior art FIG. 1, a known Ag/AgCl electrode 10 includes a rigid tube 12 within which a Ag/AgCl wire 14 is mounted by epoxy 16. The wire 14 is electrically coupled to an insulated wire lead 18 by a solder joint 20. An optional plastic cap 22 seals the upper end of the tube 12 and the wire lead 18 extends out of the end of the tube 12 through the optional cap 22. (In some known electrodes, a Ag/AgCl pellet coupled to a silver wire is used in lieu of the Ag/AgCl wire 14.) A sodium chloride liquid or gel solution 24 is provided in the lower end of the tube 12 such that the Ag/AgCl wire 14 is bathed in the solution. The solution 24 is maintained within the tube 12 by a porous glass, ceramic, or polymeric plug 26 which is press fit into the tube 12. The plug 26 allows ionic contact between the internal solution and an external solution (not shown). The nature of the porous plug 26 is such that the sodium chloride solution 24 will eventually evaporate if the electrode 10 is not kept submersed in a solution. Therefore, in order to prevent the sodium chloride solution 24 from dissipating during the time between manufacture and use of the electrode, a tightly fitting removable plastic cap 28 is provided at the lower end of the electrode 10 to cover the plug 26. (In some known electrodes, the porous plug is flush fit to the tube and held in place by heat shrink tubing.) Prior to using the electrode 10, the cap 28 must be removed and the electrode submersed in solution soon thereafter.

The prior art electrode 10 will meet the electrochemical requirements of the nitrate removal systems described above in the co-owned patent applications and will solve many of the problems associated with fresh water systems and large scale salt water systems. However, it has a significant disadvantage. Prior to first use, the user must open the nitrate removal system, locate the reference electrode, and remove the cap. This is a significant disadvantage for three reasons. First, it is time consuming, especially in closed systems where the cover of a tank must be removed. Second, since the reference electrode must be located very close to the cathode, there is not much room for manipulation of the cap to remove it. Third, removal of the cap can damage the electrode or displace the electrode away from the cathode unless great care is taken.

SUMMARY OF THE INVENTION

It is therefore an object of the invention to provide a Ag/AgCl electrode with a self-contained chloride solution or gel which does not require the removal of a cap prior to use.

It is also an object of the invention to provide methods for making a Ag/AgCl electrode with a self-contained chloride solution which does not require the removal of a cap prior to use.

It is another object of the invention to provide nitrate removal systems which incorporate a Ag/AgCl electrode with a self-contained chloride solution which does not require the removal of a cap prior to use.

In accord with these objects which will be discussed in detail below, a Ag/AgCl electrode according to the present invention includes a rigid tube within which a Ag/AgCl wire is mounted by epoxy. An insulated wire lead is coupled by a solder joint to the Ag/AgCl wire. A plastic cap seals the upper end of the tube and the wire lead extends out of the upper end of the tube and through the plastic cap. A sodium chloride liquid or gel solution is provided in the lower end of the tube such that the Ag/AgCl wire is bathed in the solution. The solution is maintained within the tube by a porous glass, ceramic, or polymeric plug which is press fit into the lower end of the tube. According to the invention, the lower end of the tube including the plug is coated with a water soluble non-toxic substance. The water soluble substance is preferably applied by dip coating and air drying. The water soluble substance forms a hard durable protective coating which prevents the sodium chloride solution from evaporating during the time between manufacture and use of the electrode. In addition, the water soluble substance quickly dissolves once in contact with flowing water. The electrode according to the invention meets all of the electrochemical requirements of the nitrate removal systems described above in the co-owned patent applications and solves the problems associated with fresh water systems and large scale salt water systems without any of the disadvantages of the prior art electrodes.

According to a presently preferred embodiment of the invention, the water soluble coating is made from a concentrated solution of polyvinyl alcohol (PVA) in deionized or RO (reverse osmosis) water. The solution is made by slowly dissolving 30–35% by weight PVA in water at 70°–80° C. with vigorous stirring. After the PVA is dissolved, the syrupy solution is allowed to stand for several hours so that air bubbles dissipate. The solution can be stored at room temperature for up to two months. The electrodes according to the invention are dipped into the prepared solution and then allowed to dry.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
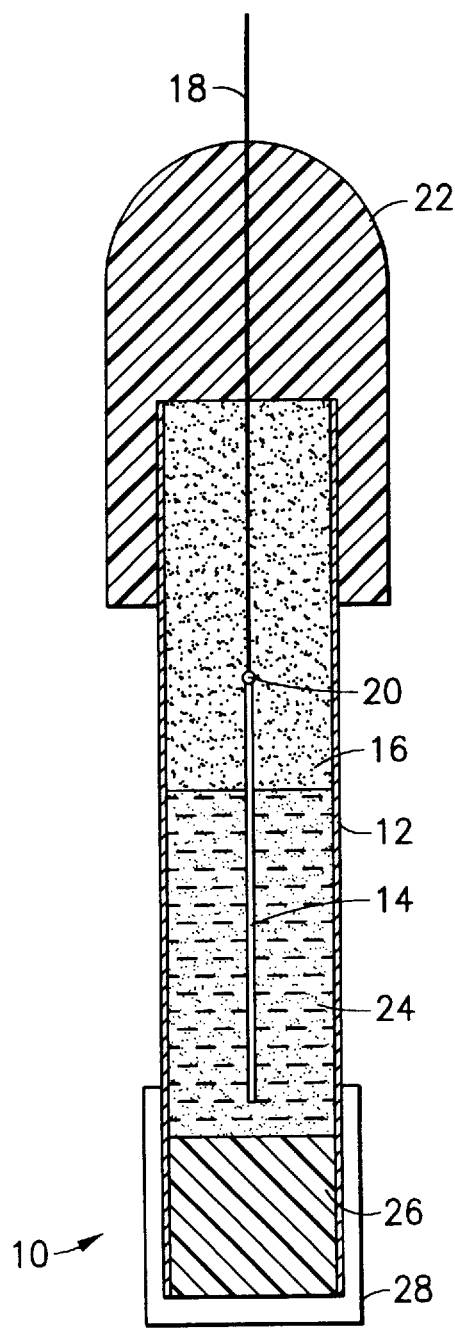
FIG. 1 is a schematic sectional view of a prior art Ag/AgCl electrode with a self-contained chloride solution.
Figure 2:
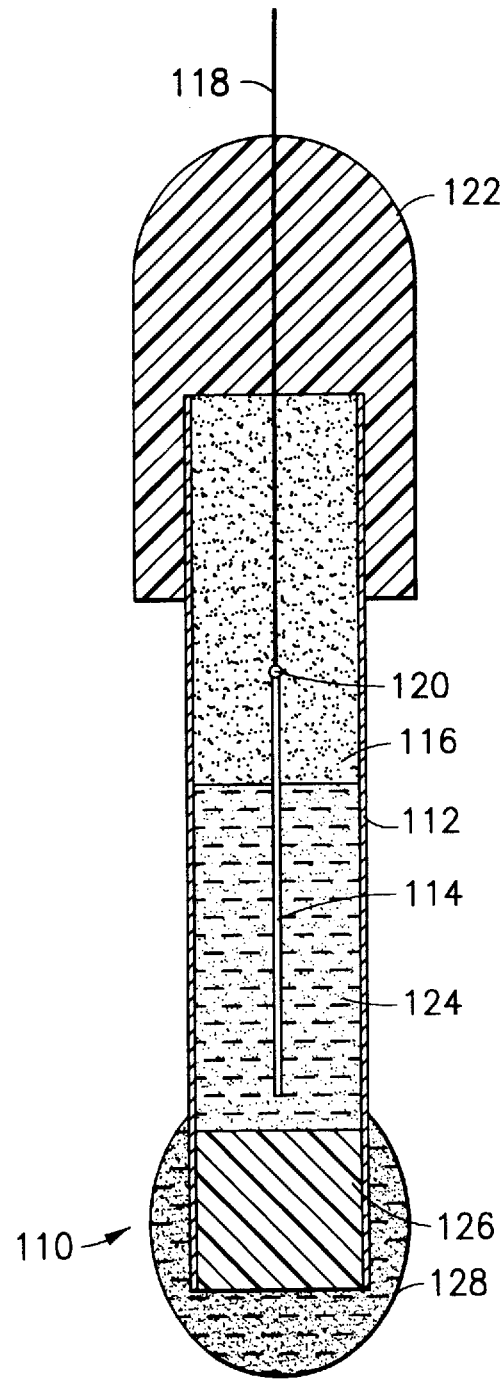
FIG. 2 is a schematic sectional view of a Ag/AgCl electrode with a self-contained chloride solution according to the invention.

Referring now to FIG. 2, a Ag/AgCl electrode 110 according to the invention includes a rigid tube 112 within which a Ag/AgCl wire 114 is mounted by epoxy 116. The Ag/AgCl wire 114 is electrically coupled to an insulated wire lead 118 by a solder joint 120. An optional plastic cap 122 seals the upper end of the tube 112 and the wire lead 118 extends out of the upper end of the tube 112 and through the cap 122. A sodium chloride liquid or gel solution 124 is provided in the lower end of the tube 112 such that the Ag/AgCl wire 114 is bathed in the solution. The solution 124 is maintained within the tube 112 by a porous glass, ceramic, or polymeric plug 126 which is press fit into the lower end of the tube 112. In order to prevent the sodium chloride solution 124 from dissipating during the time between manufacture and use of the electrode, the lower end of the tube 112 including the plug 126 is coated with a water soluble non-toxic substance 128.

According to a presently preferred embodiment of the invention, the water soluble coating is made from a concentrated solution of polyvinyl alcohol (PVA) in deionized or RO water. The presently preferred grade of PVA is 87% hydrolyzed with a molecular weight of 10,000. Other grades may also be suitable, however. The solution is made by slowly dissolving 30–35% by weight PVA in deionized or RO water at 70°–80° C. with vigorous stirring. After the PVA is dissolved, the syrupy solution is allowed to stand for several hours so that air bubbles dissipate. The solution can be stored at room temperature for up to two months. The electrodes according to the invention are dipped into the prepared solution and then allowed to dry. Drying may be accomplished in 2–3 hours at room temperature or in approximately 10 minutes at 180° in an oven. In a typical electrode having a length on the order of one inch and a diameter less than or equal to three eighths of an inch, a typical coating contains approximately 50–100 milligrams of PVA. The PVA forms a hard durable protective coating which prevents the sodium chloride solution from dissipating during the time between manufacture and use of the electrode. In addition, the PVA quickly dissolves once in contact with flowing water, typically within one to five minutes.

While the presently preferred embodiment of the invention utilizes PVA, other similar substances could be used. The following is a partial list of substances which have the potential of meeting the requirements of the invention: hydroxypropyl methyl cellulose, hydroxy ethyl cellulose, hydroxy propyl cellulose, methyl cellulose, carboxymethyl cellulose sodium salt, gelatin, polaxamer, alginic acid and alginic acid sodium salt, docusate sodium, arabic gum or acacia, povidone (polyvinyl pyrrolidone or PVP), and polyethylene glycol (PEG). Also, as mentioned above, the sodium chloride solution may be provided in gel or liquid form. For forming a gel, any gelling agent compatible with sodium chloride may be used. For example, agar, alginic acid, acacia, carboxymethyl cellulose, and hydroxy propyl cellulose are all suitable gelling agents.

There have been described and illustrated herein several embodiments of a silver/silver chloride reference electrode having a self-contained chloride solution and methods of making the same. While particular embodiments of the invention have been described, it is not intended that the invention be limited thereto, as it is intended that the invention be as broad in scope as the art will allow and that the specification be read likewise. Thus, while particular grades of PVA have been disclosed, it will be appreciated that other grades could be utilized. Also, while a particular geometry of the electrode has been shown, it will be recognized that other geometries could be used with similar results obtained. Moreover, while particular configurations have been disclosed in reference to ratios of PVA and water, it will be appreciated that other configurations could be used as well. Furthermore, while certain gelling agents have been disclosed, it will be understood that different gelling agents can achieve the same or similar function as disclosed herein. It will therefore be appreciated by those skilled in the art that yet other modifications could be made to the provided invention without deviating from its spirit and scope as so claimed.

We claim:

1. A silver/silver chloride electrode for use in an electrochemical reaction, comprising:

a) a hollow member having a first end and a second end;

b) a silver/silver chloride conductor disposed within said hollow member;

c) an electrical wire lead means for electrically coupling to said conductor and for extending out of said first end of said hollow member;

d) a liquid permeable porous plug at said second end of said hollow member, said plug having an outer surface;

e) a chloride solution disposed within said hollow member between said plug and said conductor, such that said conductor is bathed in said solution; and f) a water soluble protective coating covering said outer surface of said plug.

2. An electrode according to claim 1, wherein:
said coating covers a portion of said hollow member adjacent to said plug.

3. An electrode according to claim 1, wherein:
said coating comprises a polyvinyl alcohol.

4. An electrode according to claim 1, further comprising:
g) a cap on said first end of said hollow member for sealing said first end of said hollow member.

5. An electrode according to claim 1, wherein:
said wire lead means is electrically coupled to said silver/silver chloride conductor by a solder joint.

6. An electrode according to claim 1, wherein:
said solution is a gel.

7. An electrode according to claim 6, wherein:
said gel includes a gelling agent selected from the group consisting of agar, alginic acid, acacia, carboxymethyl cellulose, and hydroxy propyl cellulose.

8. An electrode according to claim 1, wherein:
said coating is selected from the group consisting of hydro propyl methyl cellulose, hydroxy ethyl cellulose, hydroxy propyl cellulose, methyl cellulose, carboxymethyl cellulose sodium salt, gelatin, polaxamer, alginic acid and alginic acid sodium salt, docusate sodium, arabic gum or acacia, polyvinyl pyrrolidone, and polyethylene glycol.

9. An electrode according to claim 1, wherein:
said conductor is a silver/silver chloride pellet coupled to a silver wire.

10. An electrode according to claim 1, wherein:
said conductor is a silver/silver chloride wire.

11. A method of making a silver/silver chloride electrode having a self-contained chloride solution, comprising:

a) disposing a silver/silver chloride conductor in a hollow member having a first end and a second end;

b) extending a wire lead through the first end of the hollow member and electrically coupling the wire lead to the conductor;

c) placing a chloride solution in the second end of the hollow member;

d) sealing the second end of the hollow member with a high impedance porous plug having an outer surface; and e) coating the outer surface of the plug with a water soluble protective coating.

12. A method according to claim 11, wherein:
said step of coating includes coating a portion of the hollow member adjacent to the plug.

13. A method according to claim 11, wherein:
said step of coating comprises coating with a polyvinyl alcohol.

14. A method according to claim 11, further comprising:
f) sealing the first end of the hollow member around the wire lead.

15. A method according to claim 11, wherein:
said step of extending a wire lead comprises electrically coupling a wire lead to the conductor and extending the wire lead out of the first end of the hollow member.

16. A method according to claim 11, wherein:
said step of placing a chloride solution comprises placing a chloride solution in a gel form.

17. A method according to claim 11, wherein:
said step of coating comprises coating with a coating selected from the group consisting of hydroxypropyl methyl cellulose, hydroxy ethyl cellulose, hydroxy propyl cellulose, methyl cellulose, carboxymethyl cellulose sodium salt, gelatin, polaxamer, alginic acid and alginic acid sodium salt, docusate sodium, arabic gum or acacia, polyvinyl pyrrolidone, and polyethylene glycol.

18. In an apparatus for reducing nitrates in an aqueous solution, the apparatus having a cathodic electrode, an anodic electrode, and a silver/silver chloride reference electrode having a self-contained chloride solution, the improvement comprising:
a water soluble coating on the reference electrode, the water soluble coating preventing the chloride solution from dissipating during the time between manufacture and first use of the apparatus, said coating dissolving in the aqueous solution upon first use of the apparatus.

19. The improvement according to claim 18, wherein:
said coating is a polyvinyl alcohol.

20. The improvement according to claim 18, wherein:
said coating is selected from the group consisting of hydroxypropyl methyl cellulose, hydroxy ethyl cellulose, hydroxy propyl cellulose, methyl cellulose, carboxymethyl cellulose sodium salt, gelatin, polaxamer, alginic acid and alginic acid sodium salt, docusate sodium, arabic gum or acacia, polyvinyl pyrrolidone, and polyethylene glycol.

* * * * *